United States Patent [19]

Reinmüller

[11] Patent Number: 4,713,073

[45] Date of Patent: Dec. 15, 1987

[54] PLASTIC IMPLANT

[76] Inventor: Johannes Reinmüller, An der Schanze 5, D-6500 Mainz, Fed. Rep. of Germany

[21] Appl. No.: 945,173

[22] Filed: Dec. 22, 1986

Related U.S. Application Data

[63] Continuation of Ser. No. 724,208, Apr. 17, 1985, abandoned.

[30] Foreign Application Priority Data

Aug. 17, 1983 [DE] Fed. Rep. of Germany ....... 3329733

[51] Int. Cl.⁴ .............................................. A61F 2/12
[52] U.S. Cl. ...................................................... 623/8
[58] Field of Search .............................. 623/7, 8, 11, 1; 128/1 R

[56] References Cited

U.S. PATENT DOCUMENTS

| 3,366,975 | 2/1968 | Pangman | 623/8 |
| 3,453,194 | 7/1969 | Bennet et al. | 623/1 |
| 3,934,274 | 1/1976 | Hartley, Jr. | 623/8 |

OTHER PUBLICATIONS

Jaques "The Chemical & Anticoagulant Nature of Heparin" Seminars in Thrombosis and Hemostasis 4:4 (Spring) 1978.

Primary Examiner—Richard J. Apley
Assistant Examiner—David J. Isabella
Attorney, Agent, or Firm—Felfe & Lynch

[57] ABSTRACT

Plastic implant, particularly for use in implantations for constructing or reconstructing the female breast, wherein the surface of the impant is covered over with heparin.

4 Claims, 3 Drawing Figures

PLASTIC IMPLANT

This application is a continuation of application Ser. No. 724,208, filed Apr. 17, 1985 now abandoned, which is a continuation of International Application PCT/DE 84/00171 filed Aug. 16, 1984.

Plastic implant, particularly for implantation in the chest wall of humans.

The present invention relates to a plastic implant for use in human medicine, and particularly in plastic and reconstructive surgery, which by means of a special factor acting at the surface of the implant prevents undesirable tissue reactions.

Implantations of plastics in the chest wall of humans by surgical intervention are invariably done for the purpose of constructing an underdeveloped female breast or reconstructing a female breast that had been removed by previous medical procedures. Ideally, such implantations should in their outer appearance and consistency conform to existing natural conditions.

Plastic implants are presently available from various manufacturers and largely fulfill the demands for outer appearance and consistency. The plastics used—preponderantly silicones—are as a rule not harmful to health and generally heal into the human organism.

However, as is evident from the technical literature, e.g. from Biomaterials in Reconstructive Surgery, L. R. Rubin The C. V. Mosby Company, St. Louis-Toronto-London 1983, especially chapters 33, 36 and 38 thereof, these plastic implants produce after their healing into the organism a high percentage (up to 75%!) of reactions in the tissue surrounding the same (muscles or fatty tissue), the cells of the connective tissue forming a fibrous capsule around the implant. This fibrous capsule then tends to shrinking. Due to this capsule shrinkage an all-around pressure is exerted on the implant, the latter forms into a ball and its originally existing deformability and/or elasticity are lost, i.e. superimposed by heterogeneous forces—those of the connective tissue capsule. When looked at, the breast appears to be unnaturally formed and when touched, it shows an unnatural, impact-elastic consistency.

The causes for the above described capsule formation with subsequent capsule shrinkage have so far not been scientifically found. A causal intervention in this development is therefore not known at this time.

The efforts for preventing and/or treating capsule formation and/or shrinkage are presently limited to these procedures:

(a) manual capsule bursting from outside, massage (b) surgical capsule bursting (operative intervention)

(c) administration of systemically active pharmaceuticals (tablets etc.) such as vitamin E.

(d) applying of special protective coats in the implant sheaths, which often consist of polytetrafluoroethylene, for preventing silicone leakage (since several theories see herein the cause for this undesirable development)

(e) introduction of cortisol or its derivatives (adrenocortical hormones) into the implant bearing, i.e. between the surface of the implant and the inner layer of the connective tissue capsule. The hormone can either be introduced in form of an aqueous solution into the inside of the implant and then diffuses due to the relatively low molecular weight to the surface of the implant or the implant is surrounded by a double-layer sheath. The hormone is in this case introduced between the two layers and by diffusion through the outer sheath gets to the surface of the implant. In both cases, the hormone must be added prior to insertion of the implant into the organism.

The known procedures (a) through (d) have so far not proved to be effective. The procedure (e), on the other hand, does prevent with a sufficiently high dosage of the active substance capsule formation and/or shrinkage, but then entails considerable side effects of the hormone both locally and systemically in the organism, i.e. a high percentage of additional health disturbances occur.

Object of invention is to prevent the above stated drawbacks, especially capsule formation and/or shrinkage around plastic implants, particularly in the chest wall tissue, without incurring the drawbacks (health damages) of procedure (e).

This object is achieved according to the invention in that the surface of plastic implants is coated with heparin, heparinoids, or glycoaminoglycans chemically related to heparin.

Heparin is a polymeric substance naturally occurring in the human organism. It is used in medicine for other purposes, viz. for inhibiting blood clotting, and is produced commercially by various manufacturers from animal tissue.

It is very important that breast implants be implanted only in blood-dry cavities. Insufficient stopping of blood in the creation of the implant cavity by the surgeon will invariably lead to afterbleeding into the implant bearing and hematoma formation, a very undesirable complication. This known inhibiting action of heparin on blood clotting thus had to lead the skilled in the art away from the invention, since an inhibition of blood clotting in the implant bearing had to be avoided at all costs. Surprisingly, however, no adverse effect on blood clotting could be observed with the present invention.

Surprisingly, however, by binding heparin on the implant surface the blood-clotting action of heparin can be eliminated. Instead, when used according to the invention heparin proves to be a potent inhibitor of connective tissue re-formation and thus prevents an excessive connective tissue re-formation and/or undue capsule formation.

This action of heparin was not foreseeable seeing that heparin has up till now been used clinically exclusively for inhibiting blood coagulation. As has now been found by the present invention, heparin can be used for preventing unwanted connective tissue reactions. The blood clotting inhibiting action, to the extent it can still be proved to exist, remains however of no consequence in this case, since breast implants must be used in blood-dry tissue spaces.

While specifically intended for use as breast implants, the invention is by no means limited thereto. Quite analogous problems occur also with plastic implants in other locations such as calf implants, artificial tendons on the hand made from silicone, special surgical suture material from plastic fibers, tracheal tubes and the like. In all these cases, an implant made in accordance with the present invention is able to prevent formation of granulomas.

The side effects of heparin are a function of the dose administered in a given case and concern almost exclusively the blood clotting system. Reported was furthermore an inhibition of the translation of mRNA by heparin, however only in vitro in the cell-free system. An effective antagonist for overdoses of heparin is protamine sulfate.

Heparin is broken down in the liver. A further advantage of heparin is to be seen in that it is not placenta-passable, i.e. that it cannot cause damage to the embryo in cases of pregnancy. Effects of heparin on the hormone balance of the human organism are not known to exist. Heparin has thus considerable advantages vis-a-vis adrenocortical hormones with regard to its use according to the invention.

For base implants, the known and commonly employed plastics and/or polymers are used, particularly the preponderantly used silicones. To make the implant according to the invention the heparin is so fixed on the surface of the said plastics by one of the known chemical or physical methods that the preponderant part of the surface, and preferably the entire surface, is covered by heparin.

A chemical fixation can be effected by the known methods of immobilization of heparin and other chemically related substances on solid carrier materials. Examples of suitable methods are the adhesion promotion by means of quaternary ammonium salts, preferably tridodecylmethyl ammonium chloride (TDMAC), covalent fixation by the methods known for the immobilization of natural substances that contain hydroxyl groups or sulfonate groups, cross-linkage of heparin on the surface by bifunctional reagents such as glutardialdehyde, diepoxides and the like, and ionic bonding by introduction of cationic groups on the plastic surface that are able to react with the sulfonate groups of the heparin under salt formation.

Physically, the fixation can be effected by providing a porous sheath around the actual implant, the heparin which can be present in dissolved or solid form being disposed in the space between plastic surface and porous sheath. The outer plastic sheath should thereat be porous to such an extent that the heparin, which has a molecular weight of a few thousand and about 17,000 daltons, is able to pass. Since the molecular weight exclusion limits of commercial dialysis membranes are known, appropriate sheaths can readily be selected. In this particular embodiment of the invention, the heparin can be disposed either directly between the porous sheath and the plastic surface or in the plastic itself or between the outer porous sheath and a further inner sheath that encloses the actual plastic material. If the heparin exists in solution under the porous sheath the solvent to be used is preferably a substance of higher molecular weight, which is retained by the pores in about the same way as heparin. Examples are higher polyethylene glycols, polyvinylpyrrolidone and the like.

Since heparinized surfaces of devices that are flown through by blood are known for the prevention of clot formation, proven methods are available for the purpose.

In the attached drawings.

Figure 1:
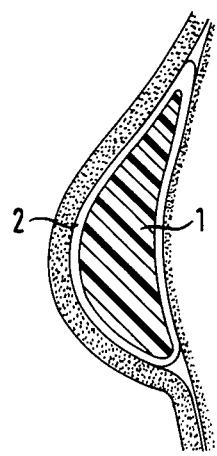
FIG. 1 shows schematically a cross section through an already implanted breast implant of plastic (1), which is covered by a layer of heparin (2).
Figure 2:
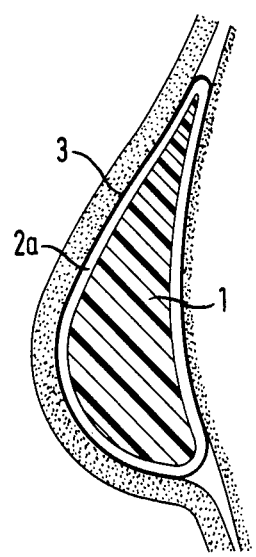
FIG. 2 shows a cross section of another embodiment of the invention, wherein the body of plastic (1) is surrounded by a heparin solution (2a) which is closed off toward the outside by a porous membrane (3).
Figure 3:
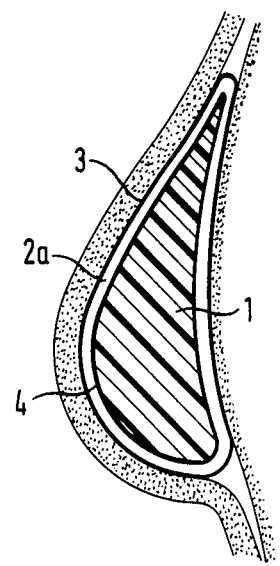
FIG. 3 shows a cross section of still another embodiment of the invention which is similar to that of FIG. 2, but additionally contains between the body of plastic (1) and the heparin solution (2a) a plastic sheath (4).

The implant of the present invention is surgically inserted in accordance with the following procedure:

Disinfection of the skin and sterile covering, incision of the skin in the armpit or in the so-called inframammary fold, cutting through the subcutaneous fatty tissue up to the fibrous membrane of the pectoral muscle (*M. pectoralis major*). A cavity is now created either above the muscle—viz between muscle and fatty tissue—or below the muscle, i.e. between the ribs and the muscles above them. The newly created cavity is inspected and bleeding stopped, damaged blood vessels are in most cases electrically heated by a special apparatus (diathermy) so that the blood in the same coagulates. As soon as the blood in the cavity has dried the implant of the invention is inserted under sterility conditions. The wound is closed with layers of surgical sutures. The above procedure is more fully described in Chir. Plastica 6, 87–93 (1981).

Within the scope of the invention, heparin can be substituted partially or wholly by other heparinoids and/or glycosaminoglycans chemically related to heparin.

The present invention makes it possible to impede the reactions of the connective tissue that may occur after implantation of plastic materials, especially into the chest wall of humans, and lead to failures in the treatment of patients. As a result, the success rate with such treatments would be improved.

The risks of additional damage to health, as with the procedures of the prior art, are also dramatically reduced.

The effectiveness of the present invention was confirmed by experimental studies on laboratory rats. The animals were narcotized and given right and left as well as left and right in random distribution through small incisions in the chest wall and on the back small silicone implants according to their size in the subcutaneous tissue, one-half of the implants containing heparin, and the other half containing no heparin. The distribution of the implants with/without heparin and right/left was purely coincidental. Each animal thus received at least two implants. The animals were kept 4, 6, 8 weeks etc. under the same conditions. The implants were then evaluated under narcosis palpatorily. The implants and the connective tissue surrounding them were then removed and microscopically examined. It was found that whenever an implant contained heparin, as contrasted with the control group that contained no heparin, capsule formation around the implants occurred only to a slight extent.

I claim:

1. A method for preventing and/or treating capsule formation and/or shrinkage around a plastic implant in a blood dry tissue cavity for construction or reconstruction of the female breast, comprising, before implanting the implant, covering and bonding to the surface of said implant, a substance selected from the group consisting of heparin, heparinoids or glycosaminoglycans chemically related to heparin.

2. The method of claim 1, wherein said substrate is bonded covalently to the surface of the implant.

3. The method of claim 1, wherein said substance is bonded ionically to the surface of the implant.

4. The method of claim 1, wherein said substance is bonded by cross-linking to the surface of the implant.

* * * * *